US008759604B2

(12) United States Patent
Brusk et al.

(10) Patent No.: US 8,759,604 B2
(45) Date of Patent: Jun. 24, 2014

(54) ABSORBENT PRODUCT

(75) Inventors: Ulla Forsgren Brusk, Pixbo (SE); Chatrine Stridfeldt, Hovås (SE); Arie Cornelis Besemer, Amerongen (NL)

(73) Assignee: SCA Hygiene Products AB, Göteborg (SE)

( * ) Notice: Subject to any disclaimer, the term of this patent is extended or adjusted under 35 U.S.C. 154(b) by 1171 days.

(21) Appl. No.: 12/096,682

(22) PCT Filed: Dec. 9, 2005

(86) PCT No.: PCT/SE2005/001884
§ 371 (c)(1),
(2), (4) Date: Jul. 21, 2008

(87) PCT Pub. No.: WO2007/067112
PCT Pub. Date: Jun. 14, 2007

(65) Prior Publication Data
US 2008/0300557 A1 Dec. 4, 2008

(51) Int. Cl.
A61F 13/15 (2006.01)
A61F 13/20 (2006.01)
A61F 13/84 (2006.01)
A61F 13/51 (2006.01)

(52) U.S. Cl.
CPC ..... *A61F 13/8405* (2013.01); *A61F 2013/8408* (2013.01); *A61F 2013/5109* (2013.01)
USPC ........................................................ 604/359

(58) Field of Classification Search
CPC .................. A61F 13/8405; A61F 2013/5109; A61F 2013/51076; A61F 2013/8508
USPC ......... 604/333, 336, 375, 359, 360, 364, 365, 604/368, 369; 502/404; 127/32, 33, 38
See application file for complete search history.

(56) References Cited

U.S. PATENT DOCUMENTS

| 3,622,460 | A   |   | 11/1971 | Masuda et al. |
| 3,881,991 | A   |   | 5/1975  | Kurimoto et al. |
| 4,323,487 | A   | * | 4/1982  | Jones et al. ................ 525/54.32 |
| 4,657,538 | A   | * | 4/1987  | Becker et al. ................ 604/381 |
| 4,985,082 | A   | * | 1/1991  | Whistler ......................... 127/33 |
| 5,051,133 | A   |   | 9/1991  | Nagai et al. |
| 5,290,269 | A   | * | 3/1994  | Heiman ........................ 604/378 |
| 5,364,380 | A   | * | 11/1994 | Tanzer et al. ................ 604/359 |
| 5,603,928 | A   | * | 2/1997  | Noda .............................. 424/76.2 |
| 5,714,445 | A   |   | 2/1998  | Trinh et al. |
| 6,147,028 | A   | * | 11/2000 | Rizzi ............................... 502/404 |
| 6,156,020 | A   | * | 12/2000 | Roe et al. ................ 604/385.01 |
| 6,229,062 | B1  |   | 5/2001  | Mandell et al. |
| 6,353,146 | B1  |   | 3/2002  | Williams |
| 6,485,733 | B1  |   | 11/2002 | Huard et al. |
| 6,653,521 | B1  | * | 11/2003 | Kurata et al. ................ 604/359 |
| 6,657,101 | B1  |   | 12/2003 | Malmgren et al. |
| 6,765,124 | B2  | * | 7/2004  | Wada et al. ................... 604/359 |
| 6,960,655 | B2  |   | 11/2005 | Di Cintio et al. |
| 2003/0114806 | A1 | * | 6/2003 | La Fortune ................... 604/359 |
| 2004/0122386 | A1 | * | 6/2004 | Mocadlo ........................ 604/359 |
| 2004/0131663 | A1 |   | 7/2004 | Walacavage et al. |
| 2005/0108828 | A1 |   | 5/2005 | Ritter |
| 2006/0239939 | A1 |   | 10/2006 | Hiramoto et al. |
| 2008/0300562 | A1 |   | 12/2008 | Ahoniemi et al. |

FOREIGN PATENT DOCUMENTS

| CN | 1314188      |     | 9/2001 |          |
| EM | 0 811 389 A1 |     | 12/1997 |         |
| EP | 0 648 116 B1 |     | 4/1995 |          |
| EP | 0 888 785 A1 |     | 1/1999 |          |
| EP | 0 894 502 A1 |     | 2/1999 |          |
| EP | 1 149 596 A1 |     | 10/2001 |         |
| JP | 61-186503    |     | 8/1986 |          |
| JP | 03-043052    |     | 2/1991 |          |
| JP | 09-030944    |     | 2/1997 |          |
| JP | 2001-145648  |     | 5/2001 |          |
| JP | 2001-231816  |     | 8/2001 |          |
| JP | 2002-369838  |     | 12/2002 |         |
| JP | 2003-154592  |     | 5/2003 |          |
| JP | 2004-148046  |     | 5/2004 |          |
| MX | PA04000086   |     | 6/2005 |          |
| WO | WO 94/01092 A1 |   | 1/1994 |          |
| WO | WO 96/09815  |     | 4/1996 |          |
| WO | WO 9609815 A1 | * | 4/1996 | ............... A61K 9/20 |
| WO | WO 98/10861  |     | 3/1998 |          |
| WO | WO 2005011836 A1 | * | 2/2005 | ............. B01D 15/08 |

OTHER PUBLICATIONS

R.P. Veregin & C.A. Fyfe, Investigation of the Crystalline "V" Amylose Complexes by High-Resolution C CP/MAS NMR Spectroscopy, 1987, American Chemical Society, Macromolecules, 20, 3007-3012.*
Eliasson, A.-C., K. Larsson, S. Andersson, S. T. Hyde, R. Nesper, and H.-G. Von Schnering. "On the Structure of Native Starch—An Analogue to the Quartz Structure." Starch—Stärke 39.5 (1987): 147-52. Print.*
Liu, Qiang., Thompson, Donald., "Effects of moisture content and different gelatinization heating temperatures on retrogradation of waxy-type maize starches." Carbohydrate Research 314 (Dec. 31, 1998): 221-235. Print.*
Schoch (Schoch, T.J. "Fractionation of Starch by Selective Precipitation with Butanol." Journal of the American Chemical Society, 64 (1942): 2957-61, ACS Publications).*

(Continued)

*Primary Examiner* — Jackie T Ho
*Assistant Examiner* — Peter S Vasat
(74) *Attorney, Agent, or Firm* — Buchanan Ingersoll & Rooney PC

(57) ABSTRACT

Absorbent product, such as a diaper, a sanitary napkin or an incontinence product, having a longitudinal and a lateral direction, including a back sheet, being distal from the body of the wearer in use of the product, and a top sheet, being proximal to the body of the wearer in use of the product, the product having a front part, a rear part and a crotch part lying between the front and rear parts, the product further including an absorbent structure, between the top and back sheet, extending longitudinally from the front part to the rear part, and whereby the product includes at least one starch-based odor control agent having a specific area of at least 5 m²/g, preferably at least 10 m²/g, more preferably at least 50 m²/g, even more preferably at least 100 m²/g, and most preferably at least 200 m²/g. Hereby, an enhanced capacity to absorb malodorous compounds of large size intervals in wet and dry systems is achieved.

25 Claims, No Drawings

(56) References Cited

OTHER PUBLICATIONS

Sarkar (A. Sarkar, S. Perez. "Discover Polysaccharides" Polysac3db (Accessed on Oct. 9, 2013 at http://polysac3db.cermay.cnrs.fr/discover_starch.html)).*

An English Translation of the Office Action (Notice of Reasons for Rejection) dated Dec. 7, 2010, issued in the corresponding Japanese Patent Application No. 2008-544289.

An English Translation of the Notification of the First Office Action issued in the corresponding Chinese Patent Application No. 200580052055.6 dated Mar. 15, 2010.

Form PCT/ISA/210 International Search Report dated Jul. 3, 2006.

Form PCT/ISA/237 (Written Opinion of the International Searching Authority) dated Jul. 3, 2006.

Austin H. Young, "Fractionation of Starch", Starch, Chemistry and Technology, Chapter 8, Starch, Second Edition, 1984, pp. 249-283, Academic Press, Inc.

J. Muetgeert, "The Fractionation of Starch", Adv. Carbohydrate Chemistry, 1961, vol. 16, pp. 299-333, Plastics Research Institute, T.N.O., Delft, Holland.

Notice of Reasons for Rejection dated Sep. 6, 2011 in JP Application No. 2008-544289.

* cited by examiner

ABSORBENT PRODUCT

TECHNICAL FIELD

This disclosure is in the field of absorbent products, such as diapers, sanitary napkins or incontinence products comprising starch-based odour control agent(s). Further this disclosure refers to the use of a starch-based odour control agent for controlling odour in an absorbent product.

TECHNICAL BACKGROUND

Odour control has become an increasingly important feature of absorbent products. Bad smells arising from secretions from the wearer of an absorbent product, or from the storing of bodily fluids within the absorbent product, give easily rise to bad odours which reduces the comfort of the wearer. Thus, it is of high importance that odours can be limited or completely prevented in absorbent products during use.

For prevention of odours one is normally focused on either (1) preventing odours from arising, or (2) preventing odours from escaping out of the absorbent product to the surrounding environment. Several different kinds of odour control agents are known for these purposes.

For instance, for masking odours, fragrances are normally used. For adsorption of odour substances, zeolites, silica, clays, active carbon and/or cyclodextrin amongst others can be used. Some of these tend however to be moisture sensitive. For neutralization of odours, baking soda, citric acid and/or acidic SAP can be used. For inhibition of bacteria growth, copper acetate, SAP with silver and/or acidic SAP can be used. Accordingly, different kinds of odour control agents are effective against different kinds of odour substances, and act with different mechanisms.

As an example EP-A-811389 discloses an absorbent article comprising an odour control system that can be chosen from e.g. silica, zeolite, absorbent gelling material, activated carbon, cyclodextrin and mixtures thereof. The odour control system may be layered on the absorbent core or be mixed within the core. Further, it can be distributed on the edges of the absorbent article.

A common problem with odour control agents is that they tend to be moisture sensitive. For instance, this is the case with zeolites and silica. Accordingly, since absorbent products absorb liquids, it is important that the parts of the absorbent products that become wet still can be effective in controlling odours.

From U.S. Pat. No. 6,147,028 it is known with an odour control agent in the form of polysiloxane-coated starch granules that is used in a sanitary napkin. Polysiloxane is considered to be the active ingredient since it provides a hydrophobic surface.

Further, US2005/0108828 discloses the use of native amylose (a fraction of starch) for odour control of e.g. tobacco or sweat in textiles. Absorbent products are not mentioned in the context of this disclosure. Further, from U.S. Pat. No. 3,622,460 it is known that starch-containing compounds have flavour-retaining properties.

Also, organic volatile substances are important to control in absorbent products, since they have undesired odours.

Moreover, U.S. Pat. No. 5,714,445 discloses articles, such as absorbent articles, comprising small-particle size cyclodextrin (a starch-based compound) for odour control. Cyclodextrin is a cyclic molecule that is composed of 1,4-alpha-linked glucose units. Cyclodextrin can be built up of 6, 7 or 8 glucose units. The inner diameter (the cavity) of cyclodextrin depends on the number of glucose units. This cavity is hydrophobic and form complexes with other substances depending on the size and hydrophobicity of the substance. Also, it will only be capable to take care of complexes when wet. The specific surface area of cyclodextrin is less than 1 $m^2/g$.

Thus, odour control agents for absorbent products need several features to be effective. Moisture-insensitivity to a certain extent, capacity to inhibit various kinds and sizes of odour compounds, not the least hydrophobic compounds, inexpensiveness, capacity to take care of malodours and environmental friendliness are some needs that should be met.

OBJECTS AND SUMMARY

Accordingly, it is an object of the disclosure to provide an absorbent product comprising at least one odour control agent that meets these demands and solves the problems as presented above.

The inventors of the present invention have discovered that a physically or physicochemically modified starch-based odour control agent having (1) an enhanced specific area of at least 5 $m^2/g$, and/or (2) wherein the starch-based odour control agent has the ability to form complexes in water, can be used in an absorbent product, and thereby a beneficial effect compared to the prior art is achieved, not the least with regard to the effectiveness of the odour control agent. The capacity to bind malodorous compounds of a large size interval is enhanced compared to the prior art.

Thus, the disclosure is directed to an absorbent product such as a diaper, a sanitary napkin or an incontinence product, having a longitudinal and a lateral direction, comprising a back sheet, being distal from the body of the wearer in use of the product, aid a top sheet, being proximal to the body of the wearer in use of the product, said product having a front part, a rear part and a crotch part lying between the front and rear parts, the product further comprising an absorbent structure, between the top and back sheet, extending longitudinally from the front part to the rear part, and whereby the product comprises at least one starch-based odour control agent, characterised in that the starch-based odour control agent has a specific area of at least 5 $m^2/g$, preferably at least 10 $m^2/g$, more preferably at least 50 $m^2/g$, even more preferably at least 100 $m^2/g$, and most preferably at least 200 $m^2/g$. Hereby, a very effective odour-control for a dry state is obtained. The ability to adsorb e.g. vapours is very high.

Preferably, the starch-based odour control agent has been physically or physicochemically modified in order to obtain an enhanced specific area. The physico-chemical treatment essentially consists of a process (which differ from material to material) leading to an enlarged surface area, followed by dewatering and fixation. For example, especially for activated starch, the physicochemical modification comprises the steps of: (a) swelling the starch-based odour control agent material in water, and (b) dewatering the material of step (a), in order to obtain a starch-based odour control agent having an enhanced specific area. Especially for amylose, the physico-chemical modification comprises the step of precipitating the starch-based odour control agent from solution with a complex forming agent. Especially for linear dextrin, the physicochemical modification comprises the step precipitating the starch-based odour control agent, either spontaneously or in the presence of a complex forming agent.

In a preferred embodiment, the starch-based odour control agent has the ability to form complexes in water, thereby being effective also in a wet state, i.e. when the active sites of the odour control agent have been inactivated or have come in contact with water.

In another preferred embodiment the starch-based odour control agent is effective in both wet and dry conditions.

In a preferred embodiment the starch-based odour control agent is chosen from amylose, preferably V-amylose, activated starch and linear dextrin. For example, V-amylose has a specific area of 20-200 m2/g and functions practically moisture-insensitive. By activating starch an enhanced surface area is achieved. Also, an enhanced surface area can be obtained for linear dextrin. Hereby, suitable for a dry system, a starch-based odour-control agent having a specific area of at least 10 m2/g, preferably 50 m2/g, more preferably 100 m2/g, and most preferably 200 m2/g is achieved.

Further, suitable for a wet system, V-amylose comprises a hydrophobic inner side in its helical structure, which further improves its capacity to adsorb hydrophobic substances. Moreover, linear dextrin is composed of a helical structure (as V-amylose) and thus has the capacity to bind hydrophobic compounds in a similar way.

In yet another preferred embodiment activated starch and/or linear dextrin and/or amylose, especially V-amylose, is positioned mainly in the dry parts of the product, thereby taking advantage of the high specific areas of these agents.

In still another preferred embodiment activated starch and/or amylose, especially V-amylose, and/or linear dextrin is positioned at positions of the product, where air mainly tend to be pressed out of the product. Hereby the agents are positioned at positions where they have a high ability to be effective, and to come in contact with malodorous gases.

In still another preferred embodiment, linear dextrin and/or amylose, especially V-amylose, is positioned mainly in the wet parts of the product, or in the wet and dry parts of the product, thereby taking advantage of the complex-forming properties and the high specific areas of these agents.

In yet another preferred embodiment, a combination of amylose, especially V-amylose, activated starch and/or linear dextrin is used.

Also, in still another preferred embodiment, further odour control agents can be used, e.g. chosen from the group of acidic SAP, cyclodextrin, activated carbon, silica and/or zeolites.

In yet another preferred embodiment the odour control agent is positioned on the top sheet and/or is positioned directly under the top sheet, and/or is positioned in the absorbent core of the product, and/or is positioned in the edges of the product, and/or is applied within the top sheet and/or is applied within or on the backing sheet of the product, or any other layer of the product.

In another aspect the disclosure relates to the use of a starch-based odour control agent having a specific area of at least 5 $m^2/g$, preferably at least 10 $m^2/g$, more preferably at least 50 $m^2/g$, even more preferably at least 100 $m^2/g$, and most preferably at least 200 $m^2/g$ for odour control in an absorbent article. Preferably, the starch-based odour control agent is chosen from at least one of amylose, preferably V-amylose, activated starch and linear dextrin.

DEFINITIONS

By a "starch-based odour control agent" is meant an odour control agent comprising, at least partly, a substance that has been derived from starch, such as natural starch, starch that has been activated, starch that has been fractionated or starch that has been modified in any way.

By a "physically or physicochemically modified" starch based odour control agent is meant a starch-based odour control agent that has been treated by way of physical or physicochemical means so that e.g. enhanced odour control properties in the form of enhanced specific area has been incurred.

By "activated starch" is meant starch granules which after swelling or treatment with suitable salts or water-miscible organic solvents have an enlarged surface area and/or enhanced adsorption properties.

By "the dry parts" and "the wet parts" of the absorbent product are meant the parts of the product that are intended to be kept dry during use (dry parts) or to absorb and/or transport liquid during use (wet parts). Hence, dry or wet conditions will mainly be present in these respective parts after liquid absorption during use.

By "specific area" or "specific surface" is meant the area (of the substance that the specific area refers to) that is available for binding of and/or interaction with other substances, or in other words: the total surface area of the particles in a gram of a substance. For measuring specific surface area, the BET-method is used. The BET-theory describes the adsorption of nitrogen molecules to a solid surface and is based upon an assumption for the energy for the adsorption of the first layer. By measuring the volume of the nitrogen gas after desorption the specific surface area is calculated. The method has been developed by Brunauer, Emmett and Teller (BET). The skilled person would know conventional instruments for performing the measurement. Alternatively, when calculating the geometrical surface area of e.g. corn starch, the dimensions and properties of corn starch (e.g. specific mass of corn starch=1500 $kg/m^3$; mass media diameter=19-20 µm; volume of a sphere=$4\pi R^3/3$; surface of a sphere is $4\pi R^2$) when it is considered as a solid sphere should be considered; i.e. 1 g starch would comprise N particles that can be considered as a (hard) sphere.

DETAILED DESCRIPTION OF THE PREFERRED EMBODIMENTS

Starch is stored in plants as a semi-crystalline granule composed of a highly ordered polymer of glucose. In most cases it is a mixture of 25% amylose and 75% amylopectin. Amylose is linear α-1,4-glucan with a few branch points, whilst amylopectin is a highly branched chain of α-1,4- and a α-1,6-glucan chains Starch (and amylose) can e.g. be obtained from plants such as Acorn, Apple, Arrowroot, Banana, Barley, waxy Barley, Easter lily, Elm, sapwood, Iris tuber, Corn (*Zea mays*), Corn of hybrid amylomaize Class V, Corn of hybrid amylomaize Class VII, Corn of hybrid waxy maize, Oat, Smooth Pea, Wrinkled Pea, Manioc, Parsnip, Potato, Rice, Waxy rice, Sago, Waxy Sorghum, Sweet potato, Tapioca and Wheat (see table 1, "Starch, Chemistry and Technology" (second edition) Ed. Whistler, BeMiller, Paschall, 1984, Chapter 8, Fractionation of starch by Austin H. Young (page 251) for further details). Corn, Wheat and Potato are the preferred starch sources.

Thus, starch consists of two fractions amylose/amylopectin. The ratio differs from source to source and variety to variety. The best examples can be found in the most widely cultured starch source, maize (corn). In the waxy variety the ratio amylopectin/amylose is 99:1. In the normal variety the ratio is 75:25 and in the high amylose variety the ratio is 25:75. Waxy varieties are among others also known for potato and rice. These starches consist also of amylopectin.

Of the two components of starch, amylose and amylopectin, amylose has the most useful functions as a hydrocolloid. Its extended conformation causes the high viscosity of water-soluble starch and varies relatively little with temperature. The extended loosely helical chains possess a relatively hydrophobic inner surface that is not able to hold water well and more hydrophobic molecules such as lipids and aroma compounds can easily replace this.

In order to obtain a starch-based odour control agent having a high specific area, the agent material is preferably modified physically or physicochemically.

Physical modifications concern mainly mechanical treatments such as grinding and milling and sometimes heating. The treatment results in modification at the surface leading to a slightly elevated surface area.

Physicochemical modification of starch granule is to allow them to swell in water, followed by dewatering. The process is conducted in such a (cautious) way that the granule remains intact. A sphere will arise consisting of holes and pores. Thus, physicochemical modification of starch, amylose and linear dextrin is a process in which the respective substrates are treated in such a way that they will adopt a high specific surface area, followed by a dewatering process to fixate this high surface area (see also example 8).

The starch-based odour control agents will work through basically two mechanisms: (1) (For a dry system) A malodour is adsorbed on a starch or a fraction thereof with an enhanced surface area. This can be achieved by swelling the starch, followed by exhaustive dewatering or drying (see e.g. example 3). (2) (For a wet system) The (hydrophobic) malodour is entrapped in the helix of amylose, especially V-amylose. In this context, amylose will also apply to short chain amylose, i.e. linear dextrins.

V-amylose is a type of amylose. V-amylose has a hydrophobic inside of its helix (suitable for a wet system). This configuration has the advantage that it can adsorb hydrophobic substances to a high degree. V-amylose has a specific area of 20-200 m2/g (suitable for a dry system).

Helical V-amylose (wherein the V stands for the German word "Verkleisterung") will in its dry state adsorb due to its enhanced surface area, whereas in the aqueous state it will adsorb due to the inclusion properties of hydrophobic substances. The properties in aqueous state can also be attributed to linear dextrins (small-sized amylose). In the wet state, V-amylose is composed of very long helices (more than 10 turns) that can entrap the malodorous compound.

V-amylose is obtained from starch by fractionation. High amylomaize starches are available from e.g. National starch; Hylon V (type A according to table 1) and Hylon VII (type B according to table 1) having 50 and 70% amylose (non-modified), respectively.

V-amylose will bind hydrophobic substances (for production of V-amylose, see the example section. Reference is also made to EP-A-648116 and U.S. Pat. No. 3,881,991, which are included as references in this disclosure) in wet systems as well as in dry systems. Amylose, a linear polymer which is a fraction of starch has some special features. Its molecular weight varies, dependent on the source, between approximately 100000 and 1000000 Da. At high temperatures it can be dissolved in water (>150° C.). When cooled to room temperature it starts to precipitate, a process known as retrogradation. This is to be expected, because the amorphous form of amylose is not soluble in water. This process can be enhanced by addition of various compounds, such as salts and water-miscible organic solvents. Magnesium sulphate leads to precipitation of an amorphous form of amylose. Contrary to this a crystalline (highly ordered form) can be obtained by using organic solvents, which leads to formation of insoluble complexes in which the amylose has adopted a helical conformation. Once freed from the complexing agent and dried, this form of amylose is cold-water soluble. In fact this structure is not quite stable, because during standing it will start to precipitate (retrograde). This process takes usually hours before any deposit is visible. After standing for one day the precipitate is complete. Despite this behaviour it is easy to isolate amylose with this conformation intact. An interesting feature is that the material is porous and has a high specific surface area. Because of the high specific surface (20 g/m$^2$-200 g/m$^2$) it is expected to bind vapours from relatively volatile materials. Details about isolation of the amylose fraction from starch can be found in Adv. Carbohydrate Chemistry, 16, 299 (1961), or from example 1.

V-amylose dissolved in water can adopt a helical configuration and especially in the presence of organic hydrophobic substances this property is enhanced. Probably the helix is induced by the hydrophobic compound because amylose adopts this configuration in which the inner side of the helix participates in hydrophobic interactions and the outer side, with its polar OH-groups, is directed to the water. In fact one can state that in the presence of a hydrophobic substance amylose coils itself round the hydrophobic substance.

The different types of amylose have very different properties (see table).

TABLE 1

| Survey of properties of different types of amylose | | | |
| --- | --- | --- | --- |
| Type | Process | Solubility in water | Specific surface area |
| A/B | Salt | Poor (<0.1 g/100 ml) | Low (<1 m$^2$/g) |
| V | Organic | Good (>1 g/100 ml) | High (20-200 m$^2$/g) |

The complex-forming properties differ between different amylose types. A/B-type will only form simple complexes on its surface. However, the V-type will dissolve and can form complexes also inside its structure.

Thus, amylose (especially the V-type) can be envisaged as an odour control agent:

In dry state the amylose will bind (organic) vapours. This property is known for substances with a relatively large specific surface area, e.g. carbon black. If amylose is located around the wet zone of a hygiene product, it will trap malodours originating from the liquid. However, if amylose becomes wetted, it will dissolve and owing to its ability to form complexes with hydrophobic materials, it will continue to trap malodours. These properties make amylose suitable as a unique odour control material, both in dry and in wet phase.

Examples of substances that can bind to amylose are e.g. 3- and 2-methylbutanal, amines, tetrahydrofuran, isovaleric acid, dimethylsulphide, octenone and octenol. These substances are very important as such with respect to odours occurring in secretions.

Activated starch can be moisture sensitive, since water-molecules tend to bind to the surface thereby occupying binding sites. It does not have a hydrophobic part (in contrast to amylose), but a high specific surface area.

Normal starch is a spherical granule with a mean diameter of 1-100 μm, relatively dense (1.5). The actual sizes and distribution depend on the source. The limited surface area (0-0.1 m2/g) reflects the fact that absorption and adsorption phenomena only play a limited role. By swelling the granule, followed by dewatering a particle arises with a much lower density and in which numerous pores are present. This material is much more active in the aspect of adsorption. Because this property is enhanced we call the starch thus obtained active or activated starch and the process to achieve this activation of starch.

Upon exposure to humid air, activated starch loses gradually its high specific surface area. However, this process is occurring only slowly.

Linear dextrin has a specific surface area of 10-60 m²/g. It is produced from amylopectin. The molecular weight is about 2000-10000. Linear dextrin is composed of 1,4-alpha-linked glucose units (like cyclodextrin). It comprises 6-7 units per turn and 2-7 turns. Basically, linear dextrin can be regarded as amylose molecules, but having a shorter chain. Linear dextrin forms a helix that can entrap hydrophobic molecules (for production of linear dextrin, see the example section. The most convenient way to prepare linear dextrins is from the fraction amylopectin In principle we can use either a waxy variety or the amylopectin fraction of any starch. An alternative is to hydrolyze amylase (Reference is also made to U.S. Pat. No. 3,881,991, which is included as a reference in this disclosure). Compared to cyclodextrin, linear dextrin has an advantage in that complex formation is more flexible due to 6-7 glucose units per turn.

TABLE 2

Comparison of starch based odour control agents of the invention.

| | Activated starch | V-amylose | Linear dextrin |
|---|---|---|---|
| Source | Starch | Starch | Amylopectin or amylose |
| Composition | Amylopectin/amylose | Amylose | Short chain amylose |
| Fraction | Not applicable | Amylose Not a natural existing fraction | Amylopectin or amylose Not a natural existing fraction |
| Molecular weight | 100 mil. -/200'-1 mil. | 100'-1 mil. | 2000-10000 |
| Surface area | 20-150 m2/g | 20-200 m2/g | 10-60 m2/g |
| Helical form | Uncertain, but likely | Yes, >10 turns (6-7 units per turn) | Yes, 2-7 turns |
| Sensitivity to water | Yes, like zeolite. | No | Will lose some activity in humid air |
| Adsorption of | Organic compounds (volatile) and water | Organic compounds Hydrophobic compounds Both gas and liquid | Hydrophobic compounds Both gas and liquid |
| Mechanism | Dry: high surface area, binding of organic volatile compounds Wet: when exposed to humidity the surface area will decrease | Dry: high surface area will bind organic vapors Wet: dissolves in water, hydrophobic interactions, will form a helix | Dry: high surface area will bind organic vapors Wet: hydrophobic interactions, will form a small helix |
| Complex forming ability | Moderate | Good | Good-moderate |

The absorbent product can be any absorbent product in which odour control is important for the use and comfort of the wearer, such as diapers, sanitary napkins, pantiliners, incontinence garments and the like.

The starch-based odour control agent of the invention can be applied to the absorbent article in several different ways. What is important is that it is applied so that it has the ability to prevent odours from arising and/or prevent gaseous odours from spreading to the surroundings of the absorbent product. The concentration that is applied for an evenly spread odour control agent, where it e.g. is glued to the backing sheet or on the material that is positioned closest to the skin, or alternatively on the wadding: 1-100 g/m2, preferably 1-50 g/m2, more preferably 1-30 g/m2. The amount of odour control agent will vary depending on e.g. the type of agent and its capacity, as well as the type and size of the product. The odour control agent can also be positioned in the beard or in the belt on a belt product, or in the standing gathers, so that the concentration is 1-200 g/m2, preferably 1-50 g/m2. Also, the odour control agent can be zoned in specifically exposed areas where the concentration of odour control agent may be as high as 2500 g/m2.

Further, as discussed above, linear dextrin and amylose are effective in both wet and dry systems, whereas activated starch is more effective in a dry system. Hence, various starch-based odour control agents can be combined in order to provide an odour control system having the advantages of both types of starch-based odour control agents. In a preferred embodiment linear dextrin and/or V-amylose, is applied to positions of the absorbent product where it will become wet; i.e. where liquid will be stored or transported. Activated starch and/or V-amylose, (due to high specific area) is applied to positions of the absorbent product that will be kept dry, and where malodorous gases can be transported out of the product; such as the backing sheet, longitudinal and lateral edges of the product, positions of the top sheet that will not become wet (i.e. not in the inlet zone) and other positions of the absorbent product.

Moreover, the starch-based odour control agent can be applied to the top sheet, where it can be applied to the whole side of the top sheet facing the wearer. It can also be applied in strings or in spots. Also, the agent can be mixed with the material of the top sheet, such as with the fibres of a nonwoven top sheet. Also, it can be applied on the side of the top sheet facing away from the wearer. Further, the odour control agent can be applied to an underlying airlaid layer or acquisition layer, or it can be applied to the absorbent core. It is also possible to apply the odour control agent to the backing sheet of the product, or to wings, standing gathers or longitudinal or lateral edges of the product, as long as it has the ability to be effective. The odour control agent can also be applied to a combination of positions. Preferably, the odour control agent is applied to the absorbent core and/or the inlet/acquisition layers or both.

The odour control agent can be applied within or on the material(s). For example, the odour control agent can be in the form of fibres having odour controlling properties. Further, the odour control agent can be sprinkled on a glue-coated surface. Also, the odour control agent can be placed in the standing gathers or in the waist elastics (for instance by clamping it between two layers in a laminate). In case the odour control agent is positioned in the waist elastics or leg elastics, it could be applied to a separate strip, or be glued to a nonwoven material that is folded to form a pocket, or it can be put in a foam structure, in the elastic thread, be coated on the fibres or on the backing sheet. Also, the odour control agent can be zoned to the parts where the malodours are likely to be transported out from the absorbent product.

The starch-based odour control agent can also be combined with one or more additional odour control agents, such as, acidic SAP, cyclodextrin, activated carbon, silica and/or zeolites. In a preferred embodiment the starch-based odour control agent is combined with acidic SAP that is positioned in the core.

The liquid-permeable top sheet is preferably made of a material showing properties like dryness and softness at use of the absorbent product, as this sheet lies against the body of the wearer. It is desired, that the sheet has a soft and textile-like surface, which remains dry also at repeated wettings. The top sheet may for example be composed of nonwoven material with a soft and smooth surface, such as for example a spunbond made of polypropylene fibres. In order to keep the surface closest to the skin of the wearer dry, a hydrophobic nonwoven-material may be used, which has holes, so that openings are formed in the material, which openings are greater than the cavities between the fibres of the material. In this way, fluid may be lead down through the holed openings in the top sheet to the underlying absorption core. Other examples of material in the top sheet may for example be holed plastic films, such as for example a holed polyethylene film. The top sheet may be connected to the underlying backing sheet and to the absorption core by, for example, glue or through some kind of thermal bonding.

The liquid-impermeable backing sheet consists of a flexible material, preferably a thin plastic film of PE (polyethylene), PP (polypropylene), a polyester, or some other kind of suitable material, such as a hydrophobic nonwoven-layer or a laminate of a thin film and a nonwoven material. These types of laminates are often used in order to achieve a soft and a textile-like surface of the backing sheet. In order to accomplish an airier and comfortable product it is also possible to use breathable backing sheets, which prevents fluid from coming out of the absorbent product, but that allows moisture to be ventilated. These breathable backing sheets may be composed of single material layers, or of laminates of, for example, blown or moulded polyethylene films, which have been laminated with, for example, a nonwoven layer of spunbond or of spunbond-meltblown-spunbond (SMS).

The absorption body is typically built up by one or more layers of cellulose fibres, for example cellulose fluff pulp. Other materials, which may be used, are for example absorbing nonwoven material, foam material, synthetic fibre materials or peat. In addition to cellulose fibres or other absorbing materials, the absorbent body may also comprise superabsorbent material, so called SAP (super absorbent polymers), that is material in the form of fibres, particles, granula, film or the like, which material has the ability to absorb fluid corresponding to several times the weight of the superabsorbent material. The superabsorbent material binds the fluid and forms a fluid-containing gel. Moreover, the absorbent body may comprise binders, form-stabilising components or the like. Additional layers improving the properties may also be used, such as various types of fluid-spreading material layers or inserts, so called waddings. The absorbent body may be chemically or physically treated in order to change the absorption properties. For instance, it is possible to provide an absorbent layer with compressed regions and/or being compressed in the entire layer(s) in order to control the fluid flow in the absorbent body. It is also possible to enclose the absorbent layer(s) in an envelope of for example tissue material.

Typically, the absorbent body has in its longitudinal direction an outstretched form, and may for example be essentially rectangular, T-shaped or hourglass-shaped. An hourglass-shaped absorbent body is wider in the front and rear parts than in the crotch part, in order to provide an efficient fluid absorption simultaneously as the design facilitates the product to form and to close around the user, thereby giving a better fit around the legs.

In order to further prevent fluid or faeces to leak out, the absorbent product on the side that is facing the wearer may also be equipped with inner fluid barriers, which are attached in connection to the longitudinal edges inside the outer barriers. Preferably, the inner barriers are made of an essentially liquid-impermeable material, such as for example a hydrophobic nonwoven or a plastic film, and are formed as a longitudinal path with a first edge being connected to the absorbent product and a second free edge, which is adapted for being in close contact with the user at use of the absorbent product. The second edge is equipped with one or more elastic elements, preferably an elastic thread, which in contracted state contracts the free edge, whereby an upstanding barrier is formed. The inner barrier may be designed as a strip of a single sheet, wherein the free edge is turned down in order to enclose the elastic element to prevent direct contact of the elastic thread to the user. Alternatively, the barrier may be formed of two combined layers, whereby the elastic thread is attached to the edge of the free end between the two layers. In this case, the inner layer of the barrier may be composed of an elongation of the top sheet and the outer layer of an essentially liquid-impermeable material, or the inner and outer layers of the barrier may be composed of one single material strip, which is folded around the elastic thread.

The rear and/or front parts of the product may also be equipped with a so called waist elastics, which is composed of elastic organs applied along the front and/or rear end edges in order to give the product a soft and flexible enclosure around the waist of the user. Suitably, the elastic organs are attached between the backing sheet and the top sheet with glue or through welding, such as ultra-sonic welding. The elastic organs may be composed of one or more elastic threads, which in a stretched state are applied between the sheets, and thereby form the waist elastics. Alternatively, the elastics may be applied between the sheets in an unstretched state, whereby both sheets instead are gathered or wrinkled at application. Another typical variant of the elastics, which is suitable, is elastic foam material composed of a thin strip of for example polyurethane foam, which like the elastic threads can be applied between the two sheets. Of course, it is also possible to position the elastic organs for the waist elastics on the outside of the backing sheet or on the inside of the top sheet.

Optionally, the absorbent product is equipped with barrier flaps (also called "standing gathers"). The main purpose of the barrier flaps is to prevent leakage of fluid from the absorbent product. Therefore, it is important that they provide a good fit to the wearer of the diaper. The barrier flaps have a proximal edge, which is close to the absorbent body and a free distal edge, which contacts the body of the user to provide the fluid barrier and also includes the elastic means.

Preferably, the barrier flaps extend along the entire length of the absorbent core, but that may in some cases not be necessary, as long as they provide a secure prevention against leakage. The height of the barrier flaps is preferably 10-50 mm, and both the proximal edge and the distal edge could be joined to the top-sheet in the front and rear ends of the product.

The barrier flaps are kept upstanding by the elastic means, which preferably runs along the distal edge inside the fold of the top sheet, which forms the flaps. This elastic means may be of any kind that is conventional in the art, and which fits into the flap.

The absorbent product may comprise a fastening system. This fastening system may be of any kind, which is suitable for the product, such as a hook and loop system, or a tape.

In yet another embodiment, the absorbent core is equipped with a wicking layer, which wicking layer has the purpose to spread fluid towards the front part of the absorbent structure. Moreover, the wicking layer does not necessarily need to cover the whole absorbent core, but should preferably cover at least the part of the absorbent core being in the front part of the casing, more preferably the part being in the front and crotch parts of the casing, and most preferably the entire absorbent core.

The wicking layer is of a moisture permeable material, preferably tissue paper or a hydrophilic non-woven, and functions to disperse the fluid, i.e. urine, passing through the liquid permeable top sheet, preferably in a direction towards the front part of the diaper. The wicking layer comprises small capillaries directing the fluid towards smaller capillaries, due to capillary forces.

EXAMPLES

Example 1

Procedure for Fractionation of Starch

General Remarks
1. This procedure can be used for different types of starch amongst others wheat, corn and potato. The A- and B-type amyloses are found in native starch granules, whereas the V-type only can be prepared by special procedures (see below). The amylose as described in the present invention concerns mainly (in a preferred embodiment) the V-type.
2. The starches mentioned contain 25% amylose (linear) and 75% amylopectin.
3. The procedures given below are examples.
   Fractionation Procedure
A. A suspension of 50 grams of starch in 1 liter aqueous magnesium sulphate solution (20%) is heated in an autoclave at 160° C. during 15 minutes. The resulting starch solution is cooled to 70° C. and the magnesium sulphate concentration is adjusted to 9.4% (w/w) and subsequently further cooled to room temperature. During the cooling process amylose precipitates. The precipitated material is isolated by centrifugation. The pellet is washed repeatedly with water until salt free, then washed twice with ethanol and finally with ether and dried. The yield is 12 grams of amorphous amylose. The amylose thus obtained can be transformed into the V-type by dissolving the amylose in water at 160° C. in the presence of a suitable complex forming agent, e.g. 2-methyl-1-butanol, followed by cooling (the further procedure is described in the example given below for the fractionation of starch by complex forming agents.
B. (alternative a) (V-type amylose) A suspension of 50 grams of starch in 1 liter of water and 200 ml 2-methyl-2-butanol is heated at 100° C. to gelatinise the starch. Then the mixture is heated in an autoclave during 15 minutes at 155° C. Upon cooling the amylose complex precipitates. By centrifugation, the amylose is separated from the amylopectin fraction, which is still in solution. The pellet is washed twice with an aqueous solution containing the complex forming agent (2-methyl-2-butanol), twice with 96% ethanol and finally with absolute ethanol. The solid is dried carefully at slightly elevated temperature in vacuum. The amylose (V-type) thus obtained has some properties required for odour adsorption in both dry and wet state.
C. (alternative b) (V-type amylose) A suspension of 50 grams of starch in 1 liter of water and 25 ml 2-methyl-1-butanol is heated at 100° C. to gelatinise the starch. Then the mixture is heated in an autoclave during 15 minutes at 155° C. Upon cooling the amylose complex precipitates. By centrifugation, the amylose is separated from the amylopectin fraction, which is still in solution. The pellet is washed twice with an aqueous solution containing 2-methyl-1-butanol at the same concentration, twice with 96% ethanol and finally with absolute ethanol. The solid is dried carefully at slightly elevated temperature in vacuum. The amylose (V-type) thus obtained has some properties required for odour adsorption in both dry and wet state.

Example 2

Binding of Acetaldehyde and Dimethylsulphide to V-Amylose

When V-amylose is exposed to the saturated atmosphere of acetaldehyde (AcH, boiling point 20° C.) and dimethylsulphide (DMS, boiling point 36° C.), the respective compounds are bound to an extent of 100%. Thus, the material can retain its own weight and this is higher than with activated starch. After exposing the charged amylose to air considerable amounts are released but even after one day 20% of AcH or DMS is still retained on the amylose.

Example 3

Preparation of Activated Starch

In this example maize starch has been used (Cas no 9005-25-8) from Sigma, art no S4126.

The maize starch is mixed with water and ethanol in the ratios: 1 part starch to 10 parts water/ethanol mixture, wherein ethanol is 20% of the liquid mixture. The entire mixture is poured into a heat-resistant vessel that is put in an oven, 100° C. for 24 hours. After 24 hours the mixture is poured in an excess of methanol in order to wash away the water that was present during preparation and stirred cautiously for 24 hours. The methanol and the residues (water and ethanol) from the preparation are filtered away. Thereafter the maize starch is "washed" yet another 24 hours with methanol.

The next step is to wash off the methanol since it may comprise water and because methanol is toxic. This is performed by the synthesis with acetone (another alternative can be to use a nonpolar solvent such as n-pentane). After all washing steps the maize starch is dried in vacuum at room temperature.

Since the maize starch tend to form lumps at the synthesis it can be beneficial to grind the sample after drying.
Results
The relatively smooth starch beads/granules have become more porous after the activation.

Example 4

Preparation of Linear Dextrin

Waxy maize starch (>99% amylopectin) is gelatinised (at 80-100° C.) or dissolved in water (>155° C.). After cooling to the temperature most suitable for the specific enzyme used, the mixture is incubated with a debranching enzyme. Specific examples of enzymes are Pseudomonas isoamylase (Hayashibara) (specific conditions: pH: 5-6; Temp: 35-40° C.) and pullulanase Promozyme (NOVO) (specific conditions: pH: 5; Temp: 55-58° C.) supplier Novozyme.

The reaction is allowed to proceed for about 24 hours. Then a solution is obtained, which consists mainly of linear dextrins. Upon heating the enzyme (protein) flocculates and can be removed by filtration, centrifugation or decantation. The resulting solution is slowly cooled to room temperature (this process usually requires >8 hours). Upon standing a precipitate is formed. After one day, the dextrins are isolated by centrifugation or filtration. The water adhering to the dextrins is removed by repeated washings with ethanol, followed by washing with absolute alcohol and drying in vacuum. An alternative method to isolate the dextrins is spray drying as mentioned in the Hayashibara patent (U.S. Pat. No. 3,622,460). This has to be conducted under careful chosen conditions i.e. inlet temperature<100° C.

Alternative preparations of the crystalline form of the dextrins include addition of complex forming agents like aliphatic alcohols (preferably butanol and higher). Use of complex forming agents makes that the cooling down after reaction is less critical.

Also the products obtained by spray drying are better (have a higher specific surface area.).

The enzyme dosage is based upon the activity of the enzyme. Usually 20 units per gram of starch are used (range between 3 and 100 units). (One unit is able to convert 1 μmol substrate per minute at optimum conditions).

Example 5

Specific Surface Area of Activated Starch Upon Exposure to Humid Air

TABLE 3

Specific surface area (m2/g) of native and activated starch upon exposure to humid air

| Exposure time (days) | Relative humidity 35% | Relative humidity 52% | Relative humidity 81% |
| --- | --- | --- | --- |
| 0 | 122 | 122 | 122 |
| 3 | 110 | 88 | 25 |
| 10 | 102 | 88 | 16 |
| 17 | 103 | 81 | 16 |
| 24 | 98 | 78 | 10 | be understood by the following reasoning: replacement of water by the water-miscible solvent, which acts a complex forming agent. Solvents such as methanol, ethanol and propanol are despite their hydrophilic character still able to form complexes provided their concentration is high enough (60, 40 and 30%, respectively). Hereby, the complex forming agent is changed. By repeating the process a few times the final result is that amylose is present in a helical form without the presence of water, but instead a volatile organic solvent in which the amylose is not soluble. By evaporation the solvent is removed. The amylose is in a helical form.

The situation with linear dextrins is somewhat different. The dextrins, prepared from amylopectin by enzymatic hydrolysis are initially soluble in water, but form upon standing a crystalline precipitate. So, there is no complex forming agent needed, contrary to the high molecular weight amylose. By careful dewatering the crystalline form with its specific properties (helix, high specific surface area) can be isolated. A very simple way to accomplish this step is spray drying, which is preferred form of drying. Details are given in the Hayashibara patent.

Activated starch with a specific surface area of 122 m2/g is exposed in a closed vessel to air of a known relative humidity. The loss of specific surface area is determined as a function of time. It follows from table 3 that the loss is slow (it takes days) and that under humid conditions, the starch still retains an appreciable amount of specific surface area.

Example 6

Adsorption of Xylene and Butanone on Starch and Carbon Black

TABLE 5

Adsorption (g/100 g substrate) of xylene and butanone on starch and carbon black.

| | Xylene | | | butanone | | |
| --- | --- | --- | --- | --- | --- | --- |
| Exposure time (hours) | Native corn starch 1 | Activated corn starch 2 | Carbon black | Native corn starch 1 | Activated corn starch 2 | Carbon black |
| 0 | 0 | 0 | 0 | 0 | 0 | 0 |
| 1 | 4 | 10 | 18 | 2 | 10 | 18 |
| 8 | 5 | 25 | 35 | 3 | 24 | 33 |
| 20 | 6 | 35 | 38 | 4 | 65 | 35 |

1 specific surface area <0.1 m$^2$/g
2 specific surface area 120 m$^2$/g

Footnote: Physicochemical modification of amylose consists of the following steps:

Conversion of amylose from its random configuration in aqueous solution into a helical form works through interaction with e.g. a hydrophobic alcohol (preferably C4) or higher complexes of amylose and the hydrophobic compound, which are insoluble in water, in other words a precipitate is formed. Dewatering the precipitated complex through a water-miscible solvent leads to fixation of the coil. It can also

The invention claimed is:

1. An absorbent product, having a longitudinal and a lateral direction, comprising a back sheet, being distal from a body of a wearer in use of the product, and a top sheet, being proximal to the body of the wearer in use of the product, said product having a front part, a rear part and a crotch part lying between the front and rear parts, the product further comprising an absorbent structure, between the top sheet and the back sheet, extending longitudinally from the front part to the rear part, and the product further comprises at least one starch-based odour control agent, and wherein the starch-based odour control agent is in helical form, wherein the starch-based odour control agent has been physicochemically modified in order to obtain an enhanced specific area, wherein the physicochemical modification comprises the step of precipitating the starch-based odour control agent from solution, wherein the starch-based odour control agent at least partly is amylose in helical form.

2. The absorbent product according to claim 1, wherein the physicochemical modification comprises the steps of: (a) swelling the starch-based odour control agent material in water, and (b) dewatering the material of step (a), in order to obtain a starch-based odour control agent having an enhanced specific area.

3. The absorbent product according to claim 1, wherein the physicochemical modification comprises the step of precipitating the starch-based odour control agent from solution with a complex forming agent.

4. The absorbent product according to claim 1, wherein the physicochemical modification comprises the step of spontaneously precipitating the starch-based odour control agent.

5. The absorbent product according to claim 1, wherein the starch-based odour control agent has the ability to form complexes in water.

6. The absorbent product according to claim 1, wherein the starch-based odour control agent is effective in both wet and dry conditions.

7. The absorbent product according to claim 1, wherein the amylose at least partly is V-amylose.

8. The absorbent product according to claim 1, wherein the starch-based odour control agent at least partly is linear dextrin in helical form.

9. The absorbent product according to claim 1, wherein the starch-based odour control agent at least partly is activated starch.

10. The absorbent product according to claim 1, whereby amylose is positioned mainly in the dry parts of the absorbent product.

11. The absorbent product according to claim 1, whereby amylose is positioned at positions of the absorbent product where air mainly tend to be pressed out of the product.

12. The absorbent product according to claim 1, wherein amylose is positioned mainly in the wet parts of the product or in both the wet and dry parts of the product.

13. The absorbent product according to claim 1, wherein the odour control agent is a combination of amylose, V-amylose, activated starch and/or linear dextrin.

14. The absorbent product according to claim 1, wherein in addition to at least one starch-based odour control agent at least one further odour control agent is used, which is chosen from the group comprising: acidic SAP, cyclodextrin, activated carbon, silica and zeolites.

15. The absorbent product according to claim 1, wherein the odour control agent is positioned on the top sheet and/or is positioned directly under the top sheet.

16. The absorbent product according to claim 1, wherein the odour control agent is positioned directly under the top sheet.

17. The absorbent product according to claim 1, wherein the odour control agent is positioned in the absorbent core of the product.

18. The absorbent product according to claim 1, wherein the odour control agent is positioned in the edges of the product.

19. The absorbent product according to claim 1, wherein the odour control agent is applied within the top sheet.

20. The absorbent product according to claim 1, wherein the odour control agent is applied within or on the backing sheet of the product.

21. The absorbent product according to claim 1, wherein the starch-based odour control agent has a specific area of at least 50 $m^2/g$.

22. The absorbent product according to claim 1, wherein the starch-based odour control agent has a specific area of at least 5 $m^2/g$.

23. The absorbent product according to claim 22, wherein the starch-based odour control agent has been physically modified in order to obtain an enhanced specific area.

24. An absorbent product, having a longitudinal and a lateral direction, comprising a back sheet, being distal from a body of a wearer in use of the product, and a top sheet, being proximal to the body of the wearer in use of the product, said product having a front part, a rear part and a crotch part lying between the front and rear parts, the product further comprising an absorbent structure, between the top sheet and the back sheet, extending longitudinally from the front part to the rear part, and the product further comprises at least one starch-based odour control agent, and wherein the starch-based odour control agent is in helical form, wherein the starch-based odour control agent has been physicochemically modified in order to obtain an enhanced specific area, wherein the physicochemical modification comprises the step of precipitating the starch-based odour control agent from solution, wherein the helical form comprises more than 10 turns.

25. An absorbent product, having a longitudinal and a lateral direction, comprising a back sheet, being distal from a body of a wearer in use of the product, and a top sheet, being proximal to the body of the wearer in use of the product, said product having a front part, a rear part and a crotch part lying between the front and rear parts, the product further comprising an absorbent structure, between the top sheet and the back sheet, extending longitudinally from the front part to the rear part, and the product further comprises at least one starch-based odour control agent, and wherein the starch-based odour control agent is in helical form, wherein the starch-based odour control agent has been physicochemically modified in order to obtain an enhanced specific area, wherein the physicochemical modification comprises the step of precipitating the starch-based odour control agent from solution, wherein the helical form comprises 2-7 turns.

* * * * *